(12) United States Patent
Gleich

(10) Patent No.: US 7,747,304 B2
(45) Date of Patent: *Jun. 29, 2010

(54) ARRANGEMENT AND METHOD FOR THE SPATIALLY RESOLVED DETERMINATION OF STATE VARIABLES IN AN EXAMINATION AREA

(75) Inventor: Bernhard Gleich, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 974 days.

This patent is subject to a terminal disclaimer.

(21) Appl. No.: 10/552,812

(22) PCT Filed: Apr. 15, 2004

(86) PCT No.: PCT/IB2004/050443

§ 371 (c)(1),
(2), (4) Date: Oct. 11, 2005

(87) PCT Pub. No.: WO2004/091386

PCT Pub. Date: Oct. 28, 2004

(65) Prior Publication Data

US 2006/0211941 A1    Sep. 21, 2006

(30) Foreign Application Priority Data

Apr. 15, 2003    (EP) .................................. 03101015

(51) Int. Cl.
*A61B 5/05* (2006.01)
(52) U.S. Cl. ...................... 600/407; 324/300; 324/307; 324/309; 600/410; 600/420; 600/424; 600/409; 607/103
(58) Field of Classification Search ................. 607/103; 600/409, 407, 410, 420, 424
See application file for complete search history.

(56) References Cited

U.S. PATENT DOCUMENTS 6,470,220 B1 * 10/2002 Kraus et al. .................. 607/103

(Continued)

FOREIGN PATENT DOCUMENTS

DE    1950474    12/1970

(Continued)

OTHER PUBLICATIONS

Daniel J. Hawrysz, et al: Developments Toward Diagnostic Breast Cancer Imaging Using Near-Infrared Optical Measurements and Fluorescent Contrast Agents, NEOPLASIA, vol. 2, No. 5, Sep.-Oct. 2000, pp. 388-417.*

*Primary Examiner*—Brian Casler
*Assistant Examiner*—John F Ramirez

(57) ABSTRACT

Examining an object wherein magnetic particles are introduced into at least part of a target area of the object under examination, the target area having a first part with a magnetic field strength that keeps magnetic particles in a non-saturated state, and a second part with a second magnetic field strength that keeps the magnetic particles in a saturated state. A superposed oscillating or rotating magnetic field is generated at least partially in the first part-area to cause at least some magnetic particles to oscillate or rotate. The target area is irradiated with electromagnetic radiation and detected radiation includes reflected or scattered electromagnetic radiation, which is modulated by interaction with rotating or oscillating magnetic particles in the target area. The intensity, absorption or polarization of the detected electromagnetic radiation is determined as a function of change in rotation or oscillation of the magnetic particles due to modulation.

25 Claims, 1 Drawing Sheet

U.S. PATENT DOCUMENTS

2003/0085703 A1   5/2003   Gleich

FOREIGN PATENT DOCUMENTS

Figure 1:
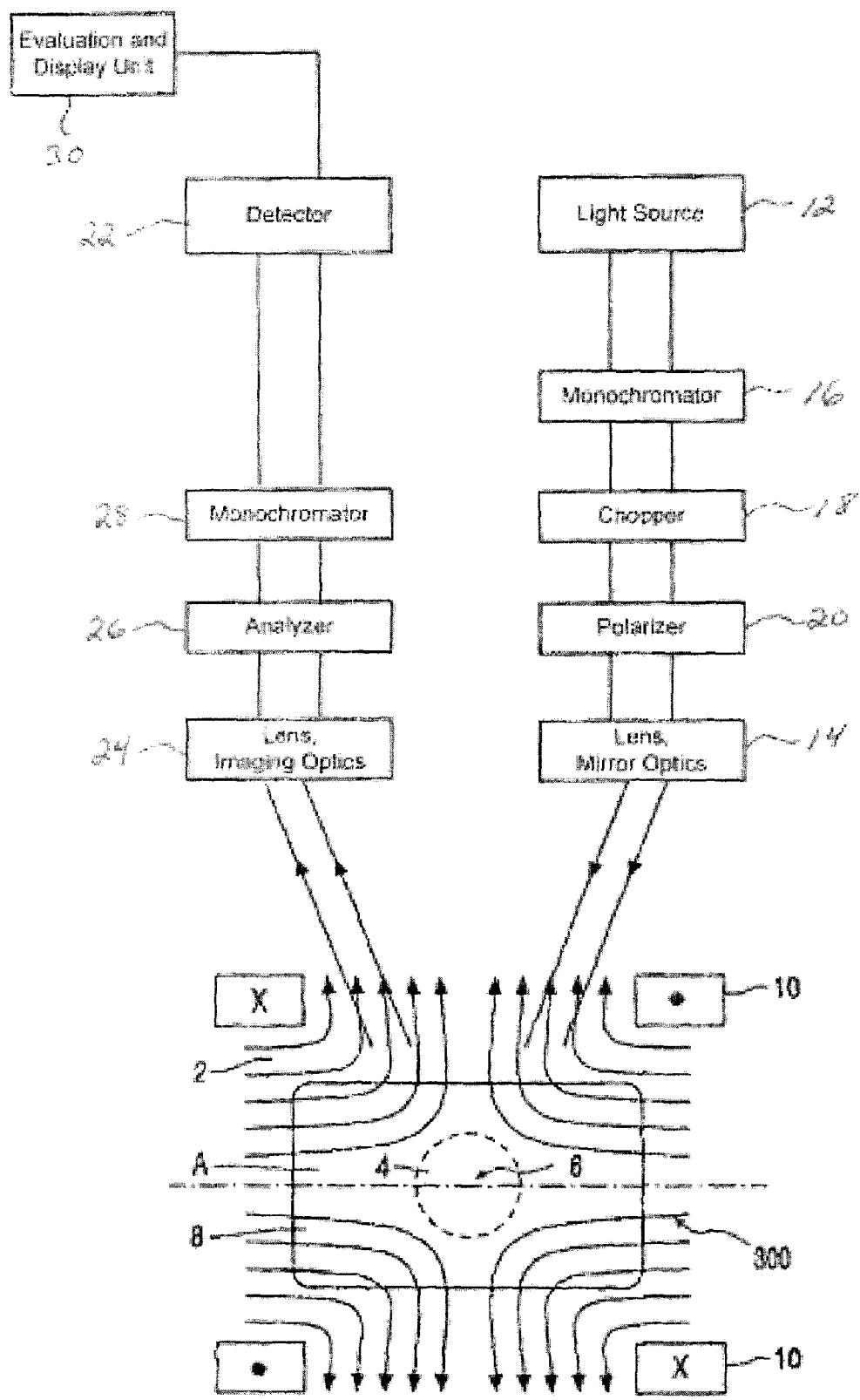

| DE | 196 24 167 A1 * | 1/1997 |
|---|---|---|
| DE | 199 30 408 A1 * | 1/2001 |
| DE | 101 51 778.5 A1 | 5/2003 |

* cited by examiner

ARRANGEMENT AND METHOD FOR THE SPATIALLY RESOLVED DETERMINATION OF STATE VARIABLES IN AN EXAMINATION AREA

The present invention relates to an arrangement for the spatially resolved determination of mechanical, physical, chemical and/or biological properties and state variables and the change in these properties and state variables in an examination area of an examination object. The present invention furthermore relates to a method for the spatially resolved determination of these properties and state variables using the arrangement according to the invention. The invention further relates to a magnetic particle composition having improved properties for magnetic particle imaging and an optical contrast composition.

In the diagnosis of tumors such as breast cancer for example, use is usually still made of the X-ray mammography imaging method even though damage to the irradiated tissue cannot be ruled out with certainty. Nuclear spin tomography, ultrasound methods and infrared tomography, which are cost-intensive and complex in terms of apparatus, are available as alternative examination methods. A particularly gentle tissue examination can be carried out with the aid of light tomography methods in which the tissue that is to be examined is illuminated with visible or infrared light and the reflected or transmitted radiation is detected.

DE 195 0 474 A1 describes an optical method which can be used to detect physiological and pathological changes in a biological tissue in vivo. In this case, tissue is irradiated with light of a specific intensity the wavelength of which is changed continuously or in discrete steps, and a transmission or reflection spectrum is recorded by measuring the intensity of the transmitted or reflected radiation as a function of the wavelength. In said method, an in vivo transmission spectrum may be recorded using a commercially available spectroradiometer which has a white light source having a uniform and high spectral radiation density, a grid monochromator, a cut-off filter and a fiber head. The radiation that is absorbed and scattered by the tissue is detected on the side opposite the glass fiber head via a fiberoptic cable.

An OCT-aided surgical system having an OCT module (Optical Coherence Tomography module), comprising a surface scanner and an evaluation and display unit, can be found in DE 199 30 408 A1. Such systems may be used for example for a navigation-assisted spinal column operation. For data generation purposes, the examination object is preferably scanned using an OCT beam in the infrared region. Nevertheless, prior to a navigation-assisted operation it is always necessary to record the examination object by means of computer tomography (CT) and to store the CT data obtained in an evaluation and display unit. According to this method it is then possible, using optical coherence tomography, to measure sectional images of biological samples and examine tissue structures up to depths of around 2 to 3 mm, with typical scanning fields making a volume of about 50 mm×50 mm×50 mm accessible for the measurement. However, larger examination areas or depth information of tissue structures are not possible using the method described in DE 199 30 408 A1.

DE 196 24 167 A1 discloses a method for coherence biometry and coherence tomography with an increased transverse resolution for measuring the position of non-reflective points along a measurement path at the surface of and inside objects by means of a measuring light beam of a short coherence interferometer. In this case, the path length comparison needed to ensure coherence with the reference light is to be effected by moving a single optical component. Using the device described in DE 196 24 167 A1, a good optical resolution is then also said to be achieved transverse to the illumination direction, said resolution in particular being constant over the entire depth of the object and free of static interference, so-called speckles. The aforementioned device is said to be particularly suitable for eye examinations.

Although light tomography methods such as optical scattering tomography have the advantage of making it possible to examine even biological tissue in a very gentle and non-destructive manner, they supply reliable data only in respect of small penetration depths in an examination object. Moreover, essentially two dimensional imaging is usually not sufficient. Furthermore, reliable imaging is often only achieved in combination with known complex examination methods such as computer tomography for example.

It would therefore be desirable to be able to make use of examination methods which do not attack or damage the object or tissue that is to be examined, regardless of the examination duration and the frequency of examinations, and at the same time supply imaging information in a manner that is simple in terms of apparatus and reliable, said imaging information not being restricted to regions of the examination object that are close to the surface.

It is therefore an object of the present invention to provide an arrangement and a method which can be used to examine examination objects in a non-destructive manner and without causing any damage, at a high resolution, both close to the surface and remote from the surface.

The object on which the method according to the invention is based is achieved by introducing magnetic particles into at least part of the examination area, generating a magnetic field with a spatial profile of the magnetic field strength such that there is produced in the examination area a first part-area having a low magnetic field strength and a second part-area having a higher magnetic field strength, generating a superposed oscillating or rotating magnetic field at least partially in the first part-area having a low magnetic field strength, so that at least some of these magnetic particles oscillate or rotate, irradiating electromagnetic radiation into the examination area by means of at least one radiation source and detecting the reflected and/or scattered electromagnetic radiation by means of at least one detector and determining the intensity, absorption and/or polarization of the reflected and/or scattered electromagnetic radiation.

It may advantageously be provided that the, in particular relative, spatial position of the two part-areas in the examination area is changed so that the magnetization of the particles changes locally, and the signals which depend on the magnetization in the examination area that is influenced by this change are detected and evaluated so as to obtain information about the spatial distribution and/or the change in the spatial distribution of the magnetic particles in the examination area.

The method according to the invention makes substantial use of an arrangement as described in the unpublished German patent application having the number 101 51 778.5 which corresponds to U.S. Patent Publication No. 2003/0085703, filed Oct. 15, 2002, which is incorporated by reference. Reference is hereby also made to the aforementioned patent application in respect of preferred embodiments of this arrangement.

A spatially inhomogeneous magnetic field is generated in the examination area by means of the arrangement used according to the invention. In the first part-area the magnetic field is so weak that the magnetization of the particles differs to a greater or lesser extent from the external magnetic field, that is to say is not saturated. This first part-area is preferably a spatially coherent area; it may also be a punctiform area or else a line or a flat area. In the second part-area (i.e. in the rest of the examination area outside the first part) the magnetic field is strong enough to keep the particles in a state of saturation. The magnetization is saturated when the magnetization of virtually all particles is aligned in approximately the direction of the external magnetic field, so that the magnetization there increases much less with a further increase in the magnetic field than in the first part-area given a corresponding increase in the magnetic field.

By changing the position of the two part-areas within the examination area, the (overall) magnetization in the examination area changes. If, therefore, the magnetization in the examination area or physical parameters influenced thereby is/are measured, information about the spatial distribution of the magnetic particles in the examination area can then be derived therefrom.

In order to change the spatial position of the two part-areas in the examination area or to change the magnetic field strength in the first part area, for example, a magnetic field that can be changed locally and/or temporally can be generated. It may also be provided that the signals induced in at least one coil by the temporal change in the magnetization in the examination area are received and evaluated in order to obtain information about the spatial distribution of the magnetic particles in the examination area. Signals that are as great as possible can be obtained by the spatial position of the two part-areas changing as rapidly as possible. A coil which is used to generate a magnetic field in the examination area can be used to detect the signals. However, at least one special coil is preferably used.

The change in the spatial position of the part-areas may also take place, for example, by means of a magnetic field that can be changed temporally. In this case a likewise periodic signal is induced in a coil. However, this signal may be difficult to receive since the signals generated in the examination area and the temporally changing magnetic field are active at the same time; it is therefore not readily possible to distinguish between the signals induced by the magnetic field and the signals induced by changing the magnetization in the examination area. However, this can be avoided by a temporally changing magnetic field acting on the examination area in a first frequency band and, from the signal received in the coil, a second frequency band which contains higher frequency components than the first frequency band being evaluated so as to obtain information about the spatial distribution of the magnetic particles. This makes use of the fact that the frequency components of the second frequency band can occur only by virtue of a change in the magnetization in the examination area as a result of the non-linearity of the magnetization characteristic. If the temporally changing magnetic field has a sinusoidal periodic profile, the first frequency band consists only of a single frequency component—the sinusoidal fundamental component. By contrast, besides this fundamental component the second frequency band also contains higher harmonics (so-called upper harmonics) of the sinusoidal fundamental component, which can be used for the evaluation.

One preferred arrangement for the method according to the invention is characterized in that the means for generating the magnetic field comprise a gradient coil arrangement for generating a magnetic gradient field which in the first part-area of the examination area reverses its direction and has a zero crossing. This magnetic field is—if the gradient coil arrangement comprises e.g. two identical windings which are arranged on either side of the examination area but which are flowed through by opposite currents (Maxwell coil)—zero at a point on the winding axis and increases virtually linearly on either side of this point with opposite polarity. Only in the case of particles which are located in the region around this field zero point is the magnetization not saturated. In respect of particles outside this area the magnetization is essentially in a state of saturation.

An arrangement may be provided with means for generating a temporally changing magnetic field that is superposed on the magnetic gradient field for the purpose of moving the two part-areas in the examination area. The area generated by the gradient coil arrangement is in this case moved around the field zero point, i.e. the first part-area, within the examination area by the temporally changing magnetic field. Given a suitable temporal profile and orientation of this magnetic field it is possible in this way for the field zero point to pass through the entire examination area.

The change in magnetization that is associated with the movement of the field zero point may be received by means of an appropriate coil arrangement. The coil used to receive the signals generated in the examination area may be a coil which is already used to generate the magnetic field in the examination area. However, there are also advantages to using a special coil for receiving, since this can be decoupled from the coil arrangement that generates a temporally changing magnetic field. Moreover, an improved signal-to-noise ratio can be achieved with one coil—but all the more so with a number of coils.

The amplitude of the signals induced in the coil arrangement is greater the quicker the position of the field zero point in the examination area changes, that is to say the quicker the temporally changing magnetic field superposed on the magnetic gradient field changes. However, it is technically difficult to generate on the one hand a temporally changing magnetic field whose amplitude is sufficient to move the field zero point to the point of the examination area and whose rate of change is sufficiently high to generate signals having a sufficient amplitude. Particularly suitable for this are those arrangements which have means for generating a first and at least a second magnetic field that are superposed on the magnetic gradient field, where the first magnetic field changes slowly in time terms and with a high amplitude and the second magnetic field changes rapidly in time terms and with a low amplitude. Two magnetic fields which change at different rates and with different amplitudes are generated—preferably by two coil arrangements. A further advantage is that the field changes may be so fast (e.g. >20 kHz) that they are above the limit of human audibility. It may likewise be provided that the two magnetic fields run essentially perpendicular to one another in the examination area. This allows the movement of the field-free point in a two-dimensional area. An expansion to a three-dimensional area is obtained by virtue of a further magnetic field which has a component that runs perpendicular to the two magnetic fields. An arrangement having a filter connected downstream of the coil arrangement is likewise advantageous, said filter suppressing from the signal induced in the coil arrangement the signal components in a first frequency band and allowing through the signal components in a second frequency band which contains higher frequency components than the first frequency component. This makes use of the fact that the magnetization characteristic in the region in which the magnetization passes from the unsaturated state to the saturated state is non-linear. This non-linearity means that a magnetic field which runs for example in a sinusoidal manner over time with the frequency f in the range of non-linearity, brings about a temporally changing induction with the frequency f (fundamental component) and integer multiples of the frequency f (upper or higher harmonics). The evaluation of the upper harmonics has the advantage that the fundamental component of the magnetic field that is active at the same time for moving the field-free point does not have any influence on the evaluation.

For the method according to the invention it is particularly advantageous if the magnetic particles are superparamagnetic particles, in particular with a low effective anisotropy, ferromagnetic monodomain particles with an effective anisotropy that is sufficient for the particles still to behave in a superparamagnetic manner only in a suspension, soft-magnetic particles, in particular having a low demagnetization factor and a magnetic anisotropy, and/or hard-magnetic particles.

Suitable magnetic particles are those which can become saturated state in the case of a sufficiently small magnetic field. A necessary prerequisite for this is that the magnetic particles have a minimum size or a minimum dipole moment.

Suitable magnetic particles advantageously have dimensions which are small compared to the size of the voxels, the magnetization of which is to be determined by means of the method according to the invention. Furthermore, the magnetization of the particles should preferably become saturated at field strengths of the magnetic field which are as low as possible. The lower the field strength necessary for this, the higher the spatial resolution capability and the weaker the (external) magnetic field that is to be generated in the examination area. Moreover, the magnetic particles should have a dipole moment that is as high as possible and a high saturation induction in order that the change in magnetization results in output signals that are as great as possible. When using the method for medical examinations, it is also important that the particles are non-toxic.

Advantageously, the magnetic particles have an anisotropy that is sufficient for the change in magnetization of the particle to take place essentially by geometric (Brown's) rotation. Although magnetization reversal via Neel's rotation may likewise occur, besides Brown's rotation it often does not make a considerable contribution to the magnetization reversal in the method according to the invention.

According to a preferred refinement of the method according to the invention it is therefore proposed that the magnetic particle is a monodomain particle the magnetization of which is reversed essentially by means of Brown's rotation.

Suitable magnetic monodomain particles are preferably dimensioned such that only a single magnetic domain (the monodomain) can form therein and a number of white regions are not present. According to a particularly preferred variant of the invention, suitable particle sizes lie in the range from 20 nm to around 800 nm, with the upper limit also depending on the material used. In respect of monodomain particles, use is preferably made of magnetite ($Fe_3O_4$), maghemite ($\gamma$-$Fe_2O_3$) and/or non-stoichiometric magnetic iron oxides. Of course it is also possible for use to be made of larger particles, e.g. having macroscopic dimensions.

In a further preferred refinement of the invention magnetic particles are used the surface of which is partially or fully reflective or is provided with a coating that reflects light or is fluorescent.

In general it is advantageous if the monodomain particles have a high effective anisotropy. The term effective anisotropy is in this case to be understood as meaning the anisotropy resulting from the form anisotropy and the crystal anisotropy. In the aforementioned case, a change in the magnetization direction requires a rotation of the particles, that is to say that the magnetization reversal upon application of an external magnetic field takes place by means of Brown's rotation or geometric rotation.

According to an alternative embodiment of the method according to the invention it may be provided that the magnetic particle is a hard- or soft-magnetic, in particular a hard-magnetic, multidomain particle. These multidomain particles are usually relatively large magnetic particles in which it is possible for a number of magnetic domains to form. Such multidomain particles advantageously have a low saturation induction.

Hard-magnetic multidomain particles essentially have the same magnetic properties as monodomain particles having a high effective anisotropy. Soft-magnetic multidomain particles with a low saturation magnetization are particularly suitable if they have an asymmetric external shape.

Suitable hard-magnetic materials comprise, for example, Al—Ni, Al—Ni—Co and Fe—Co—V alloys and also barium ferrite (BaO 6x$Fe_2O_3$).

According to the invention it is provided that the magnetic particles become saturated upon application of an external magnetic field, in particular having a strength of about 100 mT or less. Of course, greater saturation field strengths are also suitable for the method according to the invention.

For many applications, suitable magnetic field strengths are even about 10 mT or less. This strength is sufficient even for many tissue or organ examinations. However, good measurement results can also be achieved with field strengths in the region of 1 mT or less or of around 0.1 mT or less. By way of example, concentration, temperature or pH can be determined with a high degree of accuracy and definition at magnetic field strengths of around 10 mT or less, of around 1 mT or less and at around 0.1 mT or less.

Within the context of the present invention, the term external magnetic field in which the magnetic particles become saturated or are saturated is to be understood as meaning a magnetic field in which around half the saturation magnetization is achieved.

A particularly advantageous refinement of the method according to the invention is characterized in that the magnetic particles are in a liquid, viscous or gel-like shell in the examination area or are introduced into said shell.

The method according to the invention is furthermore characterized in that the electromagnetic radiation used is microwave, infrared, VIS, ultraviolet and/or X-ray radiation.

The electromagnetic radiation irradiated onto the examination object penetrates into the examination object to varying depths depending on the nature thereof and is reflected, absorbed or scattered to varying degrees in different slices of said examination object. The scattered radiation used may be for example Raleigh radiation or Mie radiation. In particular the intensity of the scattered radiation is examined in a wavelength-dependent manner.

It has furthermore proven advantageous if at least one optical contrast agent, in particular a fluorescent contrast agent, is introduced into or present in the examination area.

The optical contrast agent or fluorescent contrast agent used may be, for example, one which agglomerates or accumulates in a targeted manner in tumor tissue. By means of the method according to the invention, an imaging is then obtained which also makes three-dimensional structures clear and visible and can accordingly be used in the surgical removal of such tumors. Since the boundaries between healthy and diseased tissue can be made clearly visible, the situation is avoided whereby the healthy tissue is also attacked or parts thereof are removed at the same time.

By means of the interaction of the oscillating or rotating magnetic particles in the first part-area having a low field strength with the irradiated electromagnetic (scattered) radiation, it is possible for the tissue or tissue properties to be three-dimensionally resolved, locally delimited and imaged to a great depth with a high resolution from the detected (overall) magnetization and the, in particular wavelength-dependent, detection of the scattered and/or reflected radiation. Consequently, properties thereof can be derived in a precise manner from the magnetic and optical response signals in the examination area.

According to a further aspect of the method according to the invention it is provided that the scattered and/or reflected electromagnetic radiation is detected and evaluated in a direction-dependent manner.

Furthermore, it has also proven to be particularly expedient when the change in intensity of the scattered and/or reflected electromagnetic radiation is detected as a function of the oscillation mode or the rate of rotation.

The location of the change in intensity and the location of characteristic state variables in the examination area which interact with the irradiated electromagnetic radiation can be obtained in a particularly reliable manner when the scattered or reflected response signal can be modulated via the change in rotation or oscillation of the magnetic particles in the examination area. Depending on the orientation of the magnetic particles with respect to the irradiated light, a periodic rise or fall in the intensity of the scattered radiation can usually be ascertained as a function of the movement behavior of these particles. In this case, both the wavelength or frequency and the intensity of the irradiated light are suitable for characterizing, in particular physiological, state variables in the examination area.

It may be provided that electromagnetic radiation of at least one specific wavelength and/or wavelength spectrum is used.

A further aspect of the invention provides that the radiation source is an optical fiber or a number of optical fibers, in particular integrated in a catheter or an endoscope.

The use of, for example, optical fibers as radiation source opens up the possibility of exposing the examination object to electromagnetic radiation from inside and examining radiation, in particular scattered radiation, emerging from the object on the opposite side (the outside). In this way the sensitivity of the measurement can often be considerably improved.

By way of example, an examination object may be examined in that the part-area having a low magnetic field strength is moved by actuating and/or moving the coil arrangement or in that in the case of a stationary part-area having a low magnetic field strength the examination object is moved or in that the examination object and the part-area having a low magnetic field strength are moved relative to one another at the same time.

The object on which the arrangement according to the invention is based is achieved by an arrangement comprising a) at least one device for generating a magnetic gradient field in at least one examination area of the examination object, said device comprising a means for generating a magnetic field with a spatial profile of the magnetic field strength such that there is produced in the examination area a first part-area having a low magnetic field strength and a second part-area having a higher magnetic field strength, b) at least one radiation source for generating electromagnetic radiation and c) at least one detector for recording reflected and/or scattered electromagnetic radiation.

The arrangement for generating a magnetic gradient field essentially corresponds to that of the unpublished German patent application having the number 101 51 778.5. PW light diodes, halogen lamps, for example having a relevant measurement range of from 500 nm to 1100 nm, and conventional laser light sources are suitable by way of example as radiation sources for generating electromagnetic radiation. In respect of detectors for the recording, in particular also for the wavelength-dependent recording, of reflected and/or scattered radiation, particularly Raleigh and/or Mie radiation, use may be made of systems known to the person skilled in the art.

One advantageous arrangement further comprises a means for changing the, in particular relative, spatial position of the two part-areas in the examination area so that the magnetization of the particles changes locally, a means for detecting signals which depend on the magnetization in the examination area that is influenced by this change and a means for evaluating the signals so as to obtain information about the spatial distribution of the magnetic particles in the examination area.

It may be provided that the means for generating the magnetic field comprise a gradient coil arrangement for generating a magnetic gradient field which in the first part-area of the examination area reverses its direction and has a zero crossing.

According to a further aspect, the arrangement according to the invention has means for generating a temporally changing magnetic field that is superposed on the magnetic gradient field, for the purpose of moving the two part-areas in the examination area.

Furthermore, this arrangement may have a coil arrangement for receiving signals induced by the temporal change in the magnetization in the examination area.

Such arrangements moreover advantageously have a means for generating a first and at least a second magnetic field that are superposed on the magnetic gradient field, where the first magnetic field changes slowly in time terms and with a high amplitude and the second magnetic field changes rapidly in time terms and with a low amplitude.

It may furthermore be provided that the two magnetic fields run essentially perpendicular to one another in the examination area.

An arrangement according to the invention may moreover provide that there is at least one monochromator, chopper and/or polarizer between the radiation source and the examination area.

In the same way it may be provided that there is at least one analyzer, in particular in the form of a polarization filter, and/or one monochromator between the detector and the examination area.

An arrangement according to the invention advantageously likewise has an evaluation unit for determining and/or evaluating the detected radiation signals.

According to a further aspect of the invention it is possible that the detector is a camera or is connected to or in effective connection with the latter and/or with an evaluation unit, in particular a microprocessor.

The present invention is based on the surprising knowledge that very clear three-dimensional images having a high resolution can be generated, even away from the surface, by combining a magnetic gradient field with the irradiation of electromagnetic waves into an examination area. By way of example it is possible to precisely locate areas of tissue, for example tumor tissue, that can be delimited by means of the inventive arrangement. This may be used inter alia in order that the surrounding healthy tissue is not removed at the same time as tumor tissue. In the method according to the invention it is also advantageous that the entire frequency band of electromagnetic radiation can be used. Since, for example, Raleigh scattering and/or Mie scattering can be detected, it is possible to use known light sources and detectors, as a result of which the outlay in terms of apparatus is kept low. The frequency band for examination possibilities can be expanded even more by using optical contrast agents.

The invention will be further described with reference to an example of embodiment shown in the drawing to which, however, the invention is not restricted.

FIG. 1 schematically shows an examination object in a gradient field with a radiation and detector unit.

FIG. 1 shows an illustrative test arrangement of an examination object in a gradient field with a radiation and detector unit. In this test arrangement, the examination object 1 is located in a gradient field 2 which around the field-free point 6 has an area 4 (the first part-area) the field strength of which is so low that the magnetization of magnetic particles located there is not saturated, said area 4 being shown in dashed line. The magnetic particles present in the examination object 1 are not shown. Outside the weak-field area 4 the magnetic particles are in a state of saturation (second part-area 8). The size of the part-area 4, which determines the spatial resolution of the device, depends on the one hand on the strength of the gradient magnetic field and on the other hand on the size of the magnetic field required for saturation. A suitable magnetic field may be generated for example by way of a pair of Maxwell coils 10.

In the examination area, a further magnetic field which oscillates or rotates in at least one spatial direction is superposed on the gradient magnetic field. The fact of superposing the gradient magnetic field with a further magnetic field in principle leads to a movement of the weak-field area 4 in the direction of said magnetic field, with the extent of the movement increasing as the strength of the magnetic field increases. In the case of an oscillating or rotating magnetic field, the position of the weak-field area 4 accordingly changes temporally and locally.

Three further pairs of coils (not shown) may be provided for generating changing magnetic fields in respect of any desired direction in space. It has proven advantageous if the temporally constant gradient magnetic field and the temporally changing vertical magnetic field are generated by one and the same coil arrangement.

The light source 12 used may be for example a PW diode, a halogen lamp serving as white light source, having a relevant measurement range of from 500 nm$\leq \lambda \leq$1100 nm, or a conventional laser light source. For some applications, it has proven advantageous to provide a monochromator 16, a chopper 18 and/or a polarizer 20 in the radiation path between the light source and the lens 14. When using laser light, there is no need for the three optional components 16 to 20 mentioned above. The light radiation is directed onto the examination object 1 via suitable optics 14, with the weak-field area 4 being adjusted so that it is still in the active range of the light radiation scattered at the examination object. The magnetic particles which are oscillating or rotating in the weak-field area 4 on account of the superposed magnetic field lead to a temporally changing interaction, depending on the orientation with respect to the radiation penetrating into the examination object. If the oscillating or rotating movement behavior, for example the oscillation frequency or the rate of rotation, is known, this knowledge may be used in the evaluation of the scattered signals obtained via the detector 22. The scattered and/or reflected electromagnetic waves coming from the examination object 1 are focused onto the detector in a suitable manner via imaging optics 24 in the form of a lens. It has proven advantageous to connect therebetween one or more analyzers 26, for example polarization filters and/or monochromators 28. The light signals reaching the detector 22 may be recorded and evaluated by way of an evaluation and display unit 30 that is in effective connection with the detector.

The invention further relates to an optical contrast composition for magnetic particle imaging comprising optical contrast particles having anisotropic optical properties and which particles comprise magnetic particles or a coating of a magnetic material. The magnetic particles have a magnetic anisotropy or can be induced to have a magnetic anisotropy along a main magnetic direction in combination with a main direction of the anisotropic optical properties.

In particular, in the optical contrast composition according to the invention, the optical contrast particles have a main magnetic direction and a main optical anisotropy direction, which main magnetic direction and main optical anisotropy direction are correlated such that, when the optical contrast particles in the optical contrast composition align their main magnetic direction in an external magnetic field, their optical anisotropy direction is at least partly aligned. The optical anisotropy can be achieved in various different ways. For example, the optical contrast particles can have an anisotropic shape. Preferably, the anisotropic shape is a disc or a plate shaped. The advantage of this shape is that the particles can easily be aligned along a main optical anisotropic direction by depositing the particles on a surface. In this way, it is also easy to provide an optical active coating on only one site of the particle.

In a preferred embodiment, a part of the surface of the optical contrast particles has optical properties different from rest of the surface. Preferably, the surface of the optical contrast particles is partly coated or covered with an optically active coating material having a specific interaction with light, in particular a fluorescent material, a reflective material, a dye or a pigment.

In order to be able to rotate the optical contrast particle by means of an external magnetic field is that is preferred that in the optical contrast composition according to the invention the magnetic particles comprise anisotropic magnetic particles having an anisotropy field of at least 2 mT, so particles can rotate by applying external fields. Preferably, the anisotropy field of the magnetic particles is at least 5 mT, more preferably at least 10 mT. Preferably however the optical contrast particles also comprise soft magnetic particles, preferably isotropic magnetic particles, because these particles respond quicker to the external magnetic field and are more suitable for concentration imaging contrast improvement The invention also relates to a process for the manufacture of an optical contrast composition according to the invention, comprising aligning particles having optical anisotropic properties along a main optical anisotropy direction and depositing magnetic particles on said optical anisotropic particles in the presence of a preferably homogeneous magnetic field along a main magnetic direction. In one embodiment of the process according to the invention the anisotropic optical particles are anisotropic shaped particles, preferably disc shaped particles, which are aligned by depositing them on a surface. Another embodiment of the process comprises aligning in a magnetic field magnetic particles having magnetic anisotropic properties along a main magnetic direction and providing an optically active coating along a main optical anisotropy direction. A convenient way to achieve a main optical anisotropic direction is to deposit anisotropic shaped particles on a surface and subsequently to provide one side thereof with an optically active coating material. In a next step the magnetic particles can be deposited on the optically active coated particles in the presence of a homogeneous magnetic field.

The invention further relates to a method for imaging optical properties in an examination area comprising the steps of introducing an optical contrast composition according to the invention, irradiate the examination area with light, scanning the examination area with the field free region according to the method for magnetic particle imaging according to the invention as described above and recording reflected optical signals as a function of the position of the field free point to spatially resolve the optical properties in the examination area.

In general the magnetic particles in the magnetic particle administering composition, are chosen such that good magnetic particle images, in particular a good resolution can be obtained in a given field gradient. In unpublished German patent application number 101 51778.5 a magnetic particle imaging method is described. It is generally described that magnetic mono-domain particles having a size between 20 and 800 nanometers or a glass beat coated with a magnetic coating can be used in this method. However, in order to achieve a good magnetic imaging contrast and resolution at relatively low magnetic field gradients, improved magnetic particle compositions are highly desirable. The inventors have found magnetic particles having improved magnetic particle imaging properties.

Preferably, the magnetic particles in the magnetic particle administering composition have a magnetization curve having a step change, the step change being characterized in that the magnetization change, as measured in an aqueous suspension, in a first field strength window of magnitude delta around the inflection point of said step change is at least a factor 3 higher than the magnetization change in the field strength windows of magnitude delta below and/or in the field strength windows of magnitude delta above the first field strength window, wherein delta is less than 2000 microtesla, preferably less than 1000 microtesla, and wherein the time in which the magnetisation step change is completed in the first delta window is less than 0.01 seconds, preferably less than 0.005 sec, more preferably less than 0.001, most preferably less than 0.0005 seconds. It has been found, that such magnetic particles are particularly suitable for magnetic particle imaging, in particular for obtaining a good resolution of the image. It is further preferred, that the magnetic particle composition has a magnetisation curve, wherein the step change is at least 10%, preferably at least 20%, more preferably at least 30% and most preferably at least 50% of the total magnetisation of the particle composition as measured at an external magnetisation field of 1 Tesla. It is further preferred, that the magnetization change in the first field strength window of magnitude delta around the inflection point of said step change is at least a factor 4, preferably at least a factor 5 higher than the magnetization change in the field strength windows of magnitude delta below or in the field strength windows of magnitude delta above the first field strength window.

The magnetic particle composition is particularly useful for use in a magnetic particle imaging technique. The particles show good spatial resolution at relatively low field strength gradients. Further, the magnetic particle composition allows for a relatively high scanning speed for examining a large examination area. For example, for application in medical magnetic particle imaging, where the step change occurs preferably at a delta value below 1000 microTesla, the particle composition has a resolution value better than between 0.1 and 10 mm at magnetic field strength gradients between 10 and 0.1 T/m. With the magnetic particle imaging technique using the magnetic particle compositions according to the invention extremely good resolution can be obtained, for example in a range from 0.1 to 10 micrometers in applications, where are very high magnetic field is gradients can be achieved, for example in microscopy. It is noted that strictly speaking, magnetic field strength is expressed in H (A/m). However, in the present application, when reference is made to magnetic field strength, B-fields are meant A magnetic fields B of 2000 µT as described above corresponds to an H field of 2 mT/µ0=1.6 kA/m, that is the equivalent H field that would produce a B field of 2 mT in vacuum.

Preferably, the optical contrast composition according to the invention and the method according to the invention as described above comprise magnetic particles that meet the specified step change requirements of the magnetic particle composition according to the invention as described above.

A method for measuring the magnetisation curve and the required step change is as follows. A sample of a magnetic particle composition is suspended in water, optionally with the help of a simple detergent. To prevent clumping and/or to de-agglomerate the magnetic particles an ultrasound treatment possible can be used. The concentration of the magnetic particle composition is less than 0.01 gr core mass per liter of solvent. With core mass is meant the mass of the magnetic material in the magnetic particle composition. The suspension is brought into a fast magnetometer. (i.e. a device that measures the magnetization of the sample while an external field is applied). Suitable fast magnetometers are known to the expert. The magnetometer is equipped with means allowing to produce an external field at the sample position in at least two orthogonal directions simultaneously, i.e. to produce any magnetic field below a given maximum amplitude and a given maximum speed of change. The magnetisation is measured also in at least two orthogonal directions in the same plane.

First the saturation magnetisation is measured. For this, a magnetic field of about one Tesla is applied in one direction and the magnitude of magnetization is measured after at least 10 seconds. Then the measurement sequences for determining the step change starts. The sequence starts with choosing a field vector with an external field magnitude below 20 mT. This field is applied for at most 100 seconds. Then a second direction is chosen. This direction defines the scalar values of the field H and the magnetization M. The field is rapidly changed, preferably less than 1 millisecond, so that it lies now in −H direction with some magnitude below 20 mT. Then the field is changed from −H to +H e.g. in a linear way and the (now scalar i.e. projected) magnetization is recorded. The magnetization curve is recorded in less than 0.01 s but longer than 1 µs. Where the magnetisation curve shows a step change, a first window of size delta is positioned centrally on the inflection point of the magnetisation step change. Similarly, a window of size delta is positioned below and above the first window, and the required step change is evaluated by determining the change in magnetisation in each of the windows.

Whether or not a given magnetic particle composition has the required step change depends in a complicated way on many variables, for example of the size of the particles, the particle size distribution, the shape of the particles, the damping constant for Neel rotation, the type of magnetic material, the crystallinity and the stochiometry of the composition of the magnetic material. It has been found that it is particularly important that the particle size distribution of the particle composition is narrow. Preferably, the magnetic particle composition according to the invention has a narrow particle size distribution wherein at least 50 weight % of the particles have a particle size between plus or minus 50%, preferably 25%, more preferably 10% of the average particle size. Preferably, the amount of particles within the specified windows, is at least 70 wt %, preferably at least 80 wt %, and most preferably at least 90 wt %. Particularly good results are obtained with mono-domain particles have a low magnetic anisotropy with a field needed for inducing Neel rotation of substantially below 10 mT, preferably below 5 mT, more preferably below 2 mT. Preferably, the magnetic particles are mono-domain particles having an average particle size between 20 and 80 nanometers, more preferably between 25 and 70 nanometers, must preferably between 30 and 60 nanometers, wherein at least 50, preferably at least 60, more preferably at least 70 weight % of the particles have a particle size between the average particle size plus or minus 10 nanometer.

In an alternative embodiment of the magnetic particle composition according to the invention, the magnetic particle is a multi-domain particle having substantially a needle shape having a demagnetisation factor of less than 0.001. This magnetic particle composition is particularly useful in non-medical applications where the needles shape is not a disadvantage. In another alternative embodiment, the magnetic particle composition according to the invention comprises magnetic particles comprising a non-magnetic core covered with a magnetic coating material, wherein the thickness of the coating is between 5 and 80 nanometers and wherein the demagnetisation factor is less than 0.01 and a diameter below 300 µm. Also in these alternative embodiments it is advantageous to have a small particle size distribution as described above. The physical parameters of the magnetic particles in these embodiments are preferably chosen to meet the step change requirement as described above for achieving good imaging properties.

The magnetic particle composition according to the invention can be manufactured by first forming magnetic particles, for example by precipitation, for example by contacting a solution comprising ferrous and ferric ions with a solution comprising sodium hydroxide as described above. In principle, a known precipitation process can be used. It is also possible to grind the particles from bulk material, for example using a high speed ball mill. The essential next step for obtaining a good magnetic particle composition is the selection and separation of the particles. The first step is to perform a size selection process by filtering and/or centrifuge methods. The next step is to perform a selection process based on the magnetic properties of the particles, for example, using oscillating magnetic gradient fields.

The features of the invention that are disclosed in the above description, the claims and the drawing may be essential for the implementation of the invention in its various embodiments both individually and in any desired form.

LIST OF REFERENCES 1 arrangement
2 gradient field
4 first part-area having a low field strength
6 field-free point
8 second part-area having a higher field strength
10 pair of Maxwell coils
12 light source
14 lens, mirror optics
16 monochromator
18 chopper
20 polarizer
22 detector
24 lens, imaging optics
26 analyzer
28 monochromator
30 evaluation and display unit
A examination object

The invention claimed is:

1. A method for examining an object, the method comprising acts of:
introducing magnetic particles into at least part of a target area of an object under examination;
generating a spatially inhomogeneous magnetic field in the target area, wherein the magnetic field in a first part-area in the target area has a first magnetic field strength that keeps the magnetic particles in the first part-area in a non-saturated state, and wherein the magnetic field in a second part-area in the target area has a second magnetic field strength that keeps the magnetic particles in the second part-area in a saturated state;
generating a superposed oscillating or rotating magnetic field at least partially in the first part-area having a low magnetic field strength to cause at least some magnetic particles to oscillate or rotate;
irradiating the target area with electromagnetic radiation;
detecting electromagnetic radiation from the irradiated target area, wherein detected electromagnetic radiation includes at least one of reflected electromagnetic radiation and scattered electromagnetic radiation, which is modulated by interaction with rotating or oscillating magnetic particles in the target area; and
determining at least one of an intensity, absorption and polarization of the detected electromagnetic radiation as a function of a change in rotation or oscillation of the magnetic particles due to the modulation of the detected electromagnetic radiation.

2. The method as claimed in claim 1, comprising acts of:
changing a relative, spatial position of the first and second part-areas in the examination area to locally change a magnetization of the particles; and
detecting and evaluation signals which depend on the magnetization in the examination area that are influenced by the changing relative, spatial position of the first and second part-area to obtain information about at least one of a spatial distribution and change in the spatial distribution of the magnetic particles in the examination area.

3. The method as claimed in claim 1, wherein the magnetic particles include at least one of superparamagnetic particles with an effective anisotropy, ferromagnetic monodomain particles with an effective anisotropy sufficient for the particles to behave in a superparamagnetic manner only in a suspension, soft-magnetic particles having an anisotropy, and hard-magnetic particles.

4. The method as claimed in claim 1, wherein the magnetic particles are in a liquid, viscous or gel-like shell in the examination area or are introduced into said shell.

5. The method as claimed in claim 1, wherein the electromagnetic radiation includes at least one of microwave, infrared, VIS, ultraviolet and X-ray radiation.

6. The method as claimed in claim 1, wherein at least one optical contrast agent, in particular a fluorescent contrast agent, is introduced into or present in the examination area.

7. The method as claimed in claim 1, wherein at least one of the scattered and reflected electromagnetic radiation is detected and evaluated in a direction-dependent manner.

8. The method as claimed in claim 1, wherein determining an intensity of the detected electromagnetic radiation comprises an act of determining a change in intensity as a function of an oscillation mode or a rate of rotation.

9. The method as claimed in claim 1, wherein the examination area is irradiated with electromagnetic radiation of at least one specific wavelength or wavelength spectrum.

10. The method as claimed in claim 1, wherein the examination area is irradiated using a radiation source comprising at least one optical fiber integrated in a catheter or an endoscope.

11. The method as claimed in claim 1, comprising an act of:
moving the first part-area having a low magnetic field strength by at least one of actuating and moving a coil arrangement or when the part-area having a low magnetic field strength is stationary, moving the examination object or moving the examination object and the first part-area having a low magnetic field strength relative to one another at the same time.

12. An apparatus for examining an object, comprising:
at least one device for generating a magnetic field in a target area of an object under examination, wherein the magnetic field is a magnetic gradient field having a first magnetic field strength in a first part-area in the target area that keeps magnetic particles in the first part-area in a non-saturated state, and wherein the magnetic gradient field has a second magnetic field strength in a second part-area in the target area that keeps magnetic particles in the second part-area in a saturated state;
at least one radiation source for generating electromagnetic radiation to irradiate the target area;
at least one detector for detecting electromagnetic radiation from the irradiated target area, wherein detected electromagnetic radiation includes at least one of reflected electromagnetic radiation and scattered electromagnetic radiation, which is modulated by interaction with magnetic particles in the target area; and
an evaluation unit for processing the detected radiation signals to determine at least one property of the detected electromagnetic radiation as modulated by the interaction with the magnetic particles.

13. The apparatus as claimed in claim 12, wherein the at least one device for generating a magnetic field generates a magnetic field that changes the relative, spatial position of the first and second part-areas in the target area to locally change the magnetization of the particles, the apparatus further comprising:
a magnetic field detector for detecting signals which depend on the magnetization in the target area that are influenced by the local change; and
a second evaluating unit to evaluate the signals detected by the magnetic field detector to obtain information about the spatial distribution of the magnetic particles in the target area.

14. The apparatus as claimed in claim 12, wherein the at least one device for generating a magnetic field comprises a gradient coil arrangement for generating a magnetic gradient field in the first part-area of the target area which reverses its direction and has a zero crossing.

15. The apparatus as claimed in claim 12, wherein the at least one device for generating a magnetic field comprises a device for generating a temporally changing magnetic field that is superposed on the magnetic gradient field to change a spatial position of the first and second part-areas in the target area.

16. The apparatus as claimed in claim 12, wherein the magnetic field detector comprises a coil arrangement for receiving signals induced by the temporal change in the magnetization in the target area.

17. The apparatus as claimed in claim 12, wherein the at least one device for generating a magnetic field comprises a device for generating at least a first and second magnetic field that are superposed on the magnetic gradient field, where the first magnetic field changes slowly in time and with a high amplitude and where the second magnetic field changes rapidly in time and with a low amplitude.

18. The apparatus as claimed in claim 17, wherein the two magnetic fields run essentially perpendicular to one another in the target area.

19. The apparatus as claimed in claim 12, further comprising at least one of a monochromator, chopper and polarizer disposed between the radiation source and the target area.

20. The apparatus as claimed in claim 12, wherein the radiation source is a laser.

21. The apparatus as claimed in claim 12, further comprising at least one of an analyzer and a monochromator disposed between the at least one detector and the target area.

22. The apparatus as claimed in claim 21, wherein the analyzer is a polarization filter.

23. The apparatus as claimed in claim 12, wherein the at least one detector is a camera.

24. The apparatus as claimed in claim 12, wherein the at least one detector is coupled to at least one of a camera and the evaluation unit.

25. The apparatus as claimed in claim 24, wherein the evaluation unit comprises a microprocessor.

* * * * *